(12) United States Patent
Sablone

(10) Patent No.: US 9,498,941 B2
(45) Date of Patent: Nov. 22, 2016

(54) APPARATUS AND METHOD FOR PRODUCING A COMPOSITE ELASTICIZED WEB WITH INTERMITTENT ELASTIC SECTIONS

(71) Applicant: Fameccanica.Data S.p.A., Pescara (IT)

(72) Inventor: Gabriele Sablone, Montesilvano (IT)

(73) Assignee: Fameccanica.Data S.p.A., Pescara (IT)

( * ) Notice: Subject to any disclaimer, the term of this patent is extended or adjusted under 35 U.S.C. 154(b) by 0 days.

(21) Appl. No.: 14/955,190

(22) Filed: Dec. 1, 2015

(65) Prior Publication Data

US 2016/0159062 A1 Jun. 9, 2016

(51) Int. Cl.
| | | |
|---|---|---|
| *B32B 37/00* | (2006.01) | |
| *B32B 37/14* | (2006.01) | |
| *A61F 13/49* | (2006.01) | |
| *A61F 13/15* | (2006.01) | |
| *B32B 37/06* | (2006.01) | |

(52) U.S. Cl.
CPC ....... *B32B 37/144* (2013.01); *A61F 13/15593* (2013.01); *A61F 13/15739* (2013.01); *A61F 13/49009* (2013.01); *B32B 37/0053* (2013.01); *B32B 37/06* (2013.01); *B32B 2307/51* (2013.01)

(58) Field of Classification Search
CPC .................. A61F 13/15593; A61F 13/15739; A61F 13/49009; B32B 37/144; B32B 37/0053; B32B 37/06
USPC .......................... 156/229, 269, 494, 510, 555
See application file for complete search history.

(56) References Cited

U.S. PATENT DOCUMENTS

| | | | |
|---|---|---|---|
| 4,617,082 A | 10/1986 | Oshefsky et al. | |
| 4,692,368 A * | 9/1987 | Taylor | A61F 13/49007 156/164 |
| 2005/0101216 A1* | 5/2005 | Middlesworth | A61F 13/15577 442/394 |
| 2006/0148358 A1* | 7/2006 | Hall | B32B 5/022 442/328 |
| 2009/0326503 A1* | 12/2009 | Lakso | A61F 13/15804 604/385.23 |
| 2010/0051170 A1 | 3/2010 | Nakakado | |
| 2013/0149925 A1* | 6/2013 | Handziak | B32B 38/1875 442/1 |
| 2014/0001681 A1 | 1/2014 | Hargett et al. | |
| 2014/0338822 A1* | 11/2014 | Mukai | A61F 13/15658 156/196 |

FOREIGN PATENT DOCUMENTS

EP  0141338 A1  5/1985

OTHER PUBLICATIONS

Italian Search Report and Written Opinion dated Aug. 31, 2015 for Application No. TO2014A001015.

* cited by examiner

*Primary Examiner* — James Sells
(74) *Attorney, Agent, or Firm* — Patterson & Sheridan, LLP

(57) ABSTRACT

Apparatus for producing a composite elasticized web with intermittent elastic sections, including: a tensioning unit for tensioning in a longitudinal direction a continuous elastic film, a cutting and repitch unit comprising a knife roller and a rotary repitch device including a plurality of transport units and a plurality of anvils cooperating with the knife roller for transversely cutting the continuous tensioned elastic film and forming a succession of discrete sections of elastic film.

5 Claims, 5 Drawing Sheets

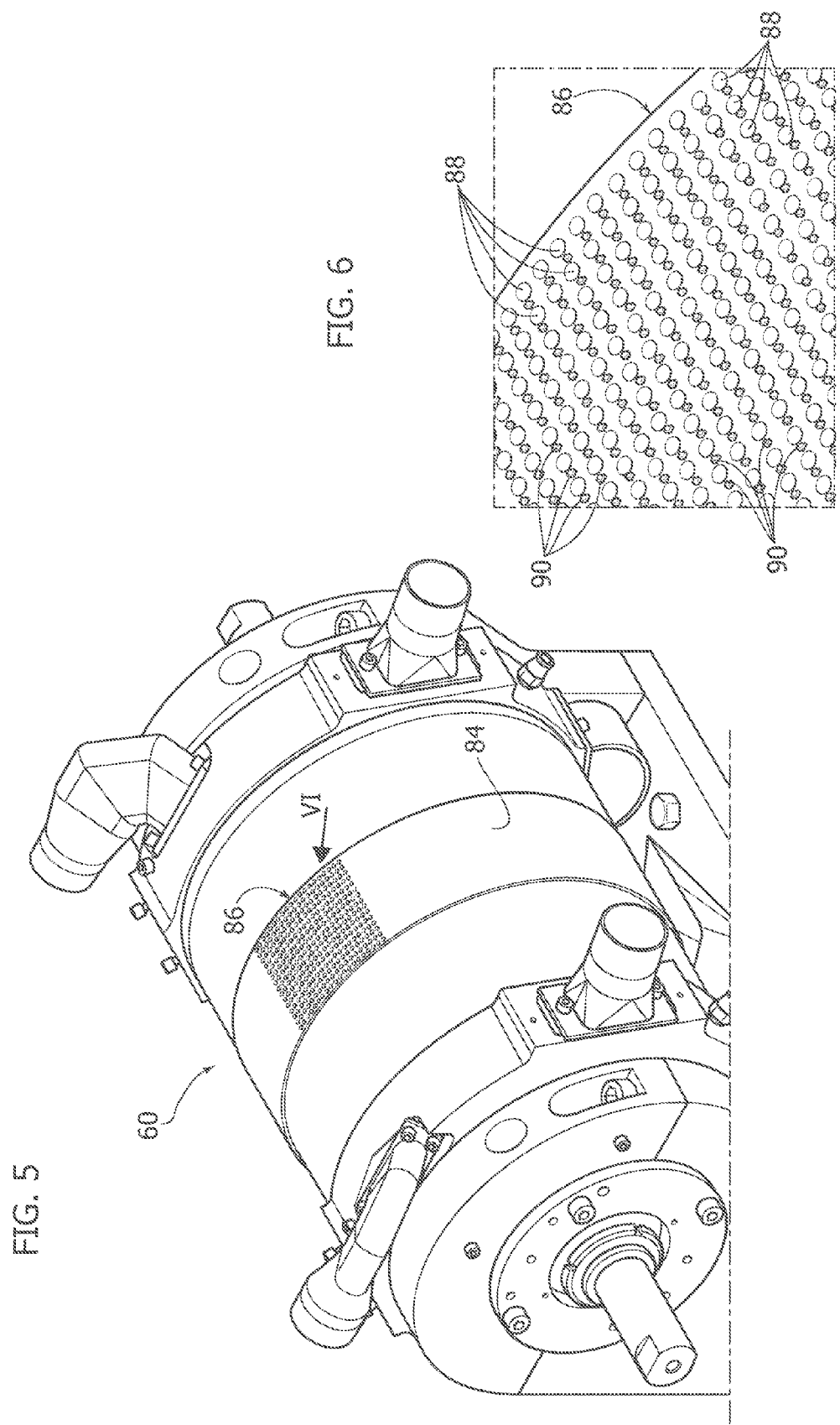

APPARATUS AND METHOD FOR PRODUCING A COMPOSITE ELASTICIZED WEB WITH INTERMITTENT ELASTIC SECTIONS

CROSS-REFERENCE TO RELATED APPLICATIONS

This application claims benefit of Italian patent application number TO2014A001015, filed Dec. 5, 2014, which is herein incorporated by reference.

BACKGROUND OF THE INVENTION

1. Field of the Invention

The present invention related to an apparatus and method for producing a composite elasticized web, with elastic sections spaced from each other by a constant pitch in the longitudinal direction of the web.

The present invention has been developed in particular for the production of elastic webs intended to be applied in the waist region of disposable absorbent sanitary articles. However, the scope of the invention is not limited to this possible field of application.

2. Description of Prior Art

Absorbent sanitary products for adults are often obtained by two continuous composite webs spaced apart in a transverse direction and advancing in the longitudinal direction, between which extend absorbent cores arranged transversely to the longitudinal direction. The composite webs form front and rear waist regions of the absorbent sanitary products. The waist regions are often provided with elastic bands in order to confer to the absorbent product improved adherence to the wearer.

An established technique for the production of elastic webs for absorbent sanitary products involves applying a continuous elastic film in a tensioned state between two webs of non-woven. In the case of absorbent products for adults it would be appreciated to have composite elastic tapes in which the elastic film is interrupted in correspondence of the absorbent core.

US2010/0051170 describes a process for producing an elasticized composite web with intermittent elastic sections. The process described in this document includes: forming sections of stretched elastic sheets starting from a continuous elastic sheet, feeding a continuous web in the longitudinal direction, applying the elastic sections intermittently on the continuous web with the stretching direction of the elastic sections aligned to the longitudinal direction of the sheet, fixing by adhesive the opposite ends of the elastic sections to the continuous web, and fixing by ultrasonic welding the elastic sections and the continuous web in intermediate areas between the opposite end portions by means of a pattern of spot welding.

SUMMARY OF THE INVENTION

The object of the present invention is to provide an apparatus and a process for producing a composite elasticized web with intermittent elastic sections that do not use adhesives.

According to the present invention, this object is achieved by an apparatus and by a method having the characteristics forming the subject of the claims 1 and 4.

The claims are an integral part of the teaching given in relation to the invention.

BRIEF DESCRIPTION OF THE DRAWINGS

The present invention will now be described in detail with reference to the accompanying drawings, given purely by way of non limiting example, in which:

FIG. 5 is a perspective view of an anvil roller indicated by the arrow V in FIG. 1.

FIG. 6 is an enlarged detail of the part indicated by the arrow VI in FIG. 5.

DETAILED DESCRIPTION

Figure 1:
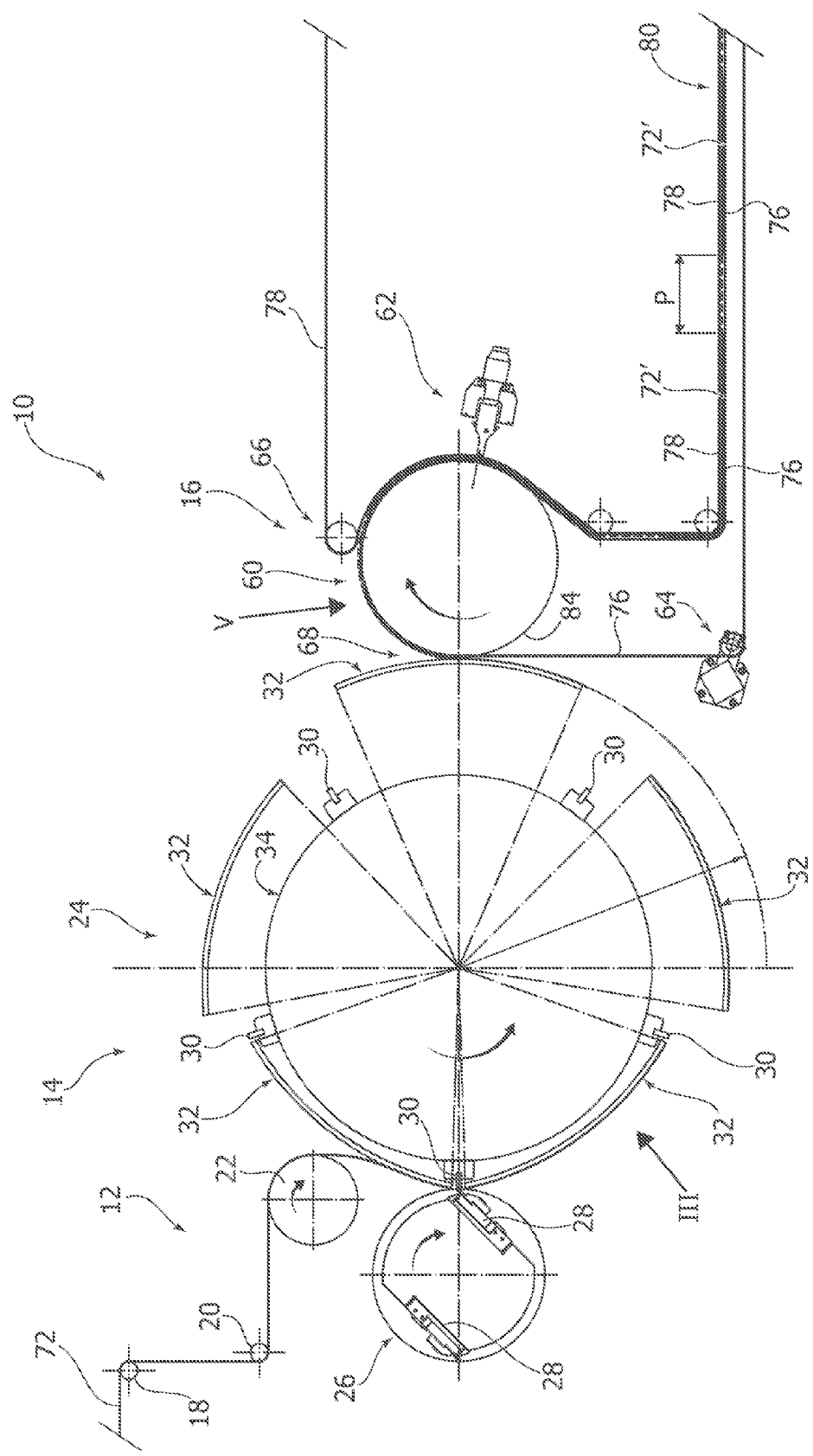
FIG. 1 is a schematic side view of an apparatus according to the present invention.
Figure 2:
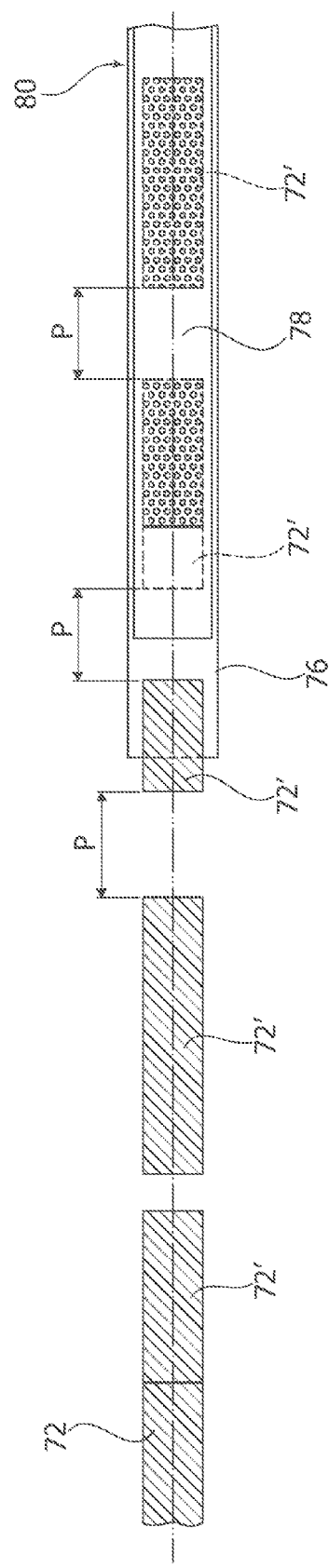
FIG. 2 is a schematic plan view showing the steps of the process according to the invention.

With reference to FIG. 1, the reference number 10 indicates an apparatus for producing a composite elasticized web used to produce waist bands of disposable absorbent sanitary products. The apparatus 10 includes a feeding and tensioning unit 12, a cutting and repitch unit 14 and a welding unit 16.

The feeding and tensioning unit 12 comprises a plurality of tensioning rollers 18, 20, 22, which may typically be independently driven, adapted to advance a continuous elastic film 72 in the longitudinal direction and to impart to the continuous elastic film 72 a longitudinal tension.

The longitudinal tension of the continuous elastic film 72 can be obtained for example by controlling the peripheral speed of the tensioning rollers 18, 20, 22, so that the tensioning rollers downstream have a peripheral speed greater than the tensioning rollers further upstream. Alternatively, the downstream tensioning roller 22 may be motorized and the tensioning rollers 18, 20 further upstream may be braked so as to impart a longitudinal tension to the continuous elastic film 72 upstream of the tensioning roller 22. The operation and control mode of the tensioning unit 12 are well known in the field of production of elasticated webs for absorbent sanitary products.

The cutting and repitch unit 14 comprises a rotary repitch device 24 and a knife roller 26. The knife roller 26 comprises one or more cutting elements 28 which cooperate with anvils 30 of the rotary repitch device 24 for transversely cutting the elastic continuous film 72 while this is kept in a tensioned state.

The rotary repitch device 24 comprises a plurality of transport units 32 carried by a rotary support 34. The anvils 30 are fixed with respect to the rotary support 34. In the shown embodiment the transport units are rotationally fixed relative to the rotary support 34 and are movable in the radial direction between a gripping position and a release position. In the release position the transport units 32 are moved radially outwardly with respect to the gripping position. During the rotation the grip units 32 move cyclically between the gripping position and the release position. A rotary repitch device of this type is described for example in U.S. Pat. No. 4,617,082. A repitch device of this type is not imperative. Any other device adapted to space from each other of a predetermined pitch subsequent discrete elements could be used.

Figure 3:
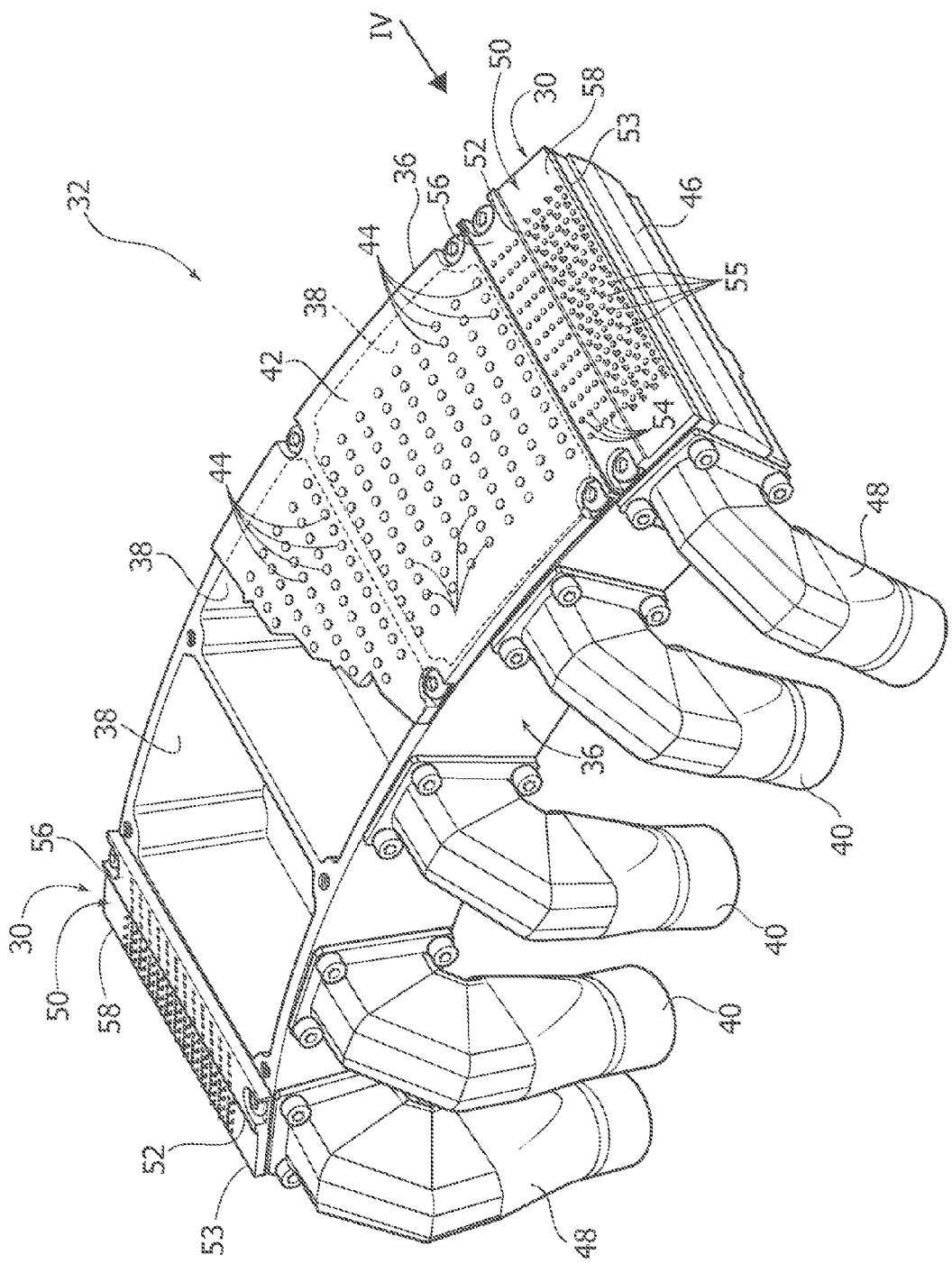
FIG. 3 is a perspective view of a transport unit indicated by the arrow III in FIG. 1.
Figure 4:
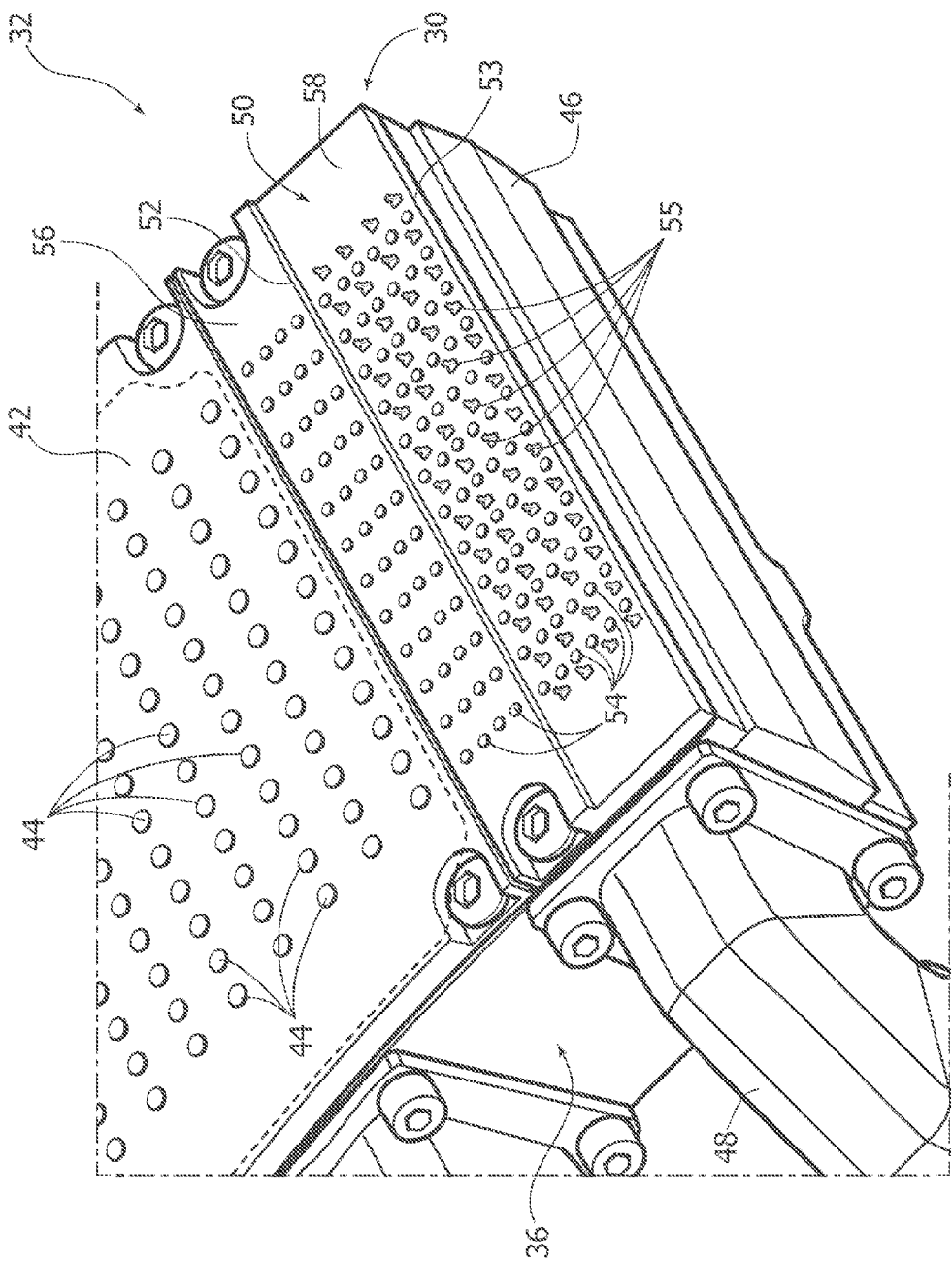
FIG. 4 is an enlarged detail of the part indicated by the arrow IV in FIG. 3.

With reference to FIG. 3, each transport unit 32 comprises a body 36 having a plurality of suction chambers 38 which communicate with a source of sub-atmospheric pressure by means of respective ducts 40. The upper part of the suction chamber 38 is closed by a cylindrical surface 42 provided with holes 44. Each transport unit 32 has substantially the shape of a cylindrical sector with an angular extension equal to the angular distance between two adjacent anvils 30. Each anvil 30 comprises a hollow body 46 connected to the source of sub-atmospheric pressure through a respective conduit 48. The body 46 has two specular end surfaces 50, each of which is typically provided with a gripping surface 58 delimited in the longitudinal direction by a transverse groove 52 and by an end edge 53 of the transport unit 32. The transverse groove 52 divides each end surface 50 in a first section 56 and in the gripping surface 58. Each end surface 50 is provided with holes 54. Preferably, the first section 56 of each end surface 50 is smooth, while the gripping surface 58 is provided with projecting teeth 55.

The welding unit 16 comprises an anvil roller 60 with an aspirating surface and an ultrasonic welding head 62 cooperating with the outer surface of the anvil roller 60. The apparatus 10 also comprises a first feeding system 64 and a second feeding system 66, to feed on the outer surface of the anvil roller 60, respectively, a first web material 76 and a second web material 78. The two web materials 76 and 78 may preferably be continuous nonwoven sheets.

With reference to FIG. 5, the anvil roller 60 has a cylindrical contact surface 84 provided with one or more suction sections 86. Each section 86 is provided with suction holes 88 which communicate with a vacuum cavity connected to a source of sub-atmospheric pressure. In the case where more suction sections 86 are provided, these are spaced apart by a pitch equal to the desired pitch between subsequent elastic sections. Each suction section 86 has a length equal to the length of a stretched elastic section. The surface 84, in the portions between two consecutive suction sections 86, may be devoid of suction holes 88.

Each suction section 86 of the anvil surface 84 is provided with protruding teeth 90 evenly distributed on the suction section 86. The projecting teeth 90 have end surfaces that form counter-sealing surfaces cooperating with the sonotrode of the ultrasonic welding head 62. Preferably, the teeth 90 have a rhomboidal cross section. The teeth 90 are preferably intercalated with the holes 88. In the shown example, the holes 88 and protruding teeth 90 are aligned in parallel transverse rows. The teeth 90 and the holes 88 alternate with each other in each transverse row.

The operation of the apparatus 10 is as follows.

The continuous elastic film 72 is subjected to a longitudinal tensioning in the feeding and tensioning unit 12 and is fed in a stretched state to a transport unit 32 of the repitch device 24. The head portion of the continuous elastic film 72 is retained by suction by the transport unit 32. The projecting teeth 55 of the gripping surface 58 facilitate gripping of the head portion of the film 72. The longitudinal tension applied to the continuous elastic film 72 by the tensioning unit 12 is maintained during transfer of the head portion of the continuous elastic film 72 from the last roller 22 of the tensioning unit 12 to the transport unit 32.

While the head portion of the continuous elastic film 72 is held in a tensioned state on the surface of the transport unit 32 of the repitch device 24, the knife roller 26 transversally cuts the continuous elastic film 72 on an anvil 30 of the repitch device 24. In this way, on the transport unit 32 of the repitch device 24 subsequent discrete sections of elastic film 72' are formed. The discrete sections of elastic film 72' are held in a tensioned state on the respective transport unit 32.

During the rotation of the repitch device 24 discrete sections of elastic film 72' are spaced apart from each other by a predetermined distance P.

The transport units 32 in the release position pass through a tangency zone 68, in which the outer surface of each transport unit 32 is tangent to the outer surface 84 of the anvil roller 60. In the tangency zone 68 discrete sections of elastic film 72' are transferred from the transport unit 32 to the anvil roller 60 of the welding unit 16. The discrete sections of elastic film 72' are kept tensioned in the longitudinal direction during the transfer from the transport unit 32 to the anvil roller 60.

The first continuous nonwoven web 76 is fed on the outer surface of the anvil roller 60 upstream of the tangency zone 68. The first continuous nonwoven web 76 is thus disposed between the outer cylindrical surface 84 of the anvil roller 60 and the discrete sections of elastic film 72'. The discrete sections of elastic film 72' are positioned on respective suction sections 68 where they are held by suction. The first continuous nonwoven web 76 is porous and, therefore, does not hinder the operations of transferring and retaining by suction the discrete sections of elastic film 72'. The protruding teeth 90 arranged on the suction sections 86 of the anvil roller 60 in cooperating positions, typically interleaved, with the suction holes 88, hold in a tensioned state discrete sections of elastic film 72' without the need to apply glue between discrete sections of elastic film 72' and the first continuous nonwoven web 76. On the anvil roller 60 discrete sections of elastic film 72' are spaced by a pitch P equal to the pitch between the transport units 32 of the repitch device 24 in the tangency zone 68.

Subsequently, the second continuous nonwoven web 78 is fed on the cylindrical surface 84 of the anvil roller 60 downstream of the tangency zone 68. In this way, the two web materials 76 and 78 comprise between them the discrete sections of elastic film 72'.

Downstream of the feeding zone of the second continuous nonwoven web 78 to the anvil roller 60, the welding head 62 performs the welding of the first continuous nonwoven web 76, the discrete sections of elastic film 72' and the second continuous nonwoven web 78 on the head surfaces of the protruding teeth 90.

In areas where the discrete sections of elastic film 72' are spaced apart, the welding head 62 welds to each other the first continuous nonwoven web 76 and the second continuous nonwoven web 78 on the head surfaces of the protruding teeth 90.

The product which is obtained downstream of the welding head 62 is a continuous composite tape 80 with discrete sections of elastic film 72' tensioned in the longitudinal direction and spaced at a predetermined pitch P. The discrete sections of elastic film 72' are sandwiched between the two continuous nonwoven webs 76, 78. A particularly important feature of the present invention is that the discrete sections of elastic film 72' are fixed to the two continuous sheets 76, 78 exclusively by welding, without any use of glue. With the solution according to the present invention it is possible to avoid the use of glue in view of the fact that the discrete sections of elastic film 72' are applied directly to the suction sections 86 of the anvil roll 60 equipped with projecting teeth 90 that form the counter-sealing surfaces on which the welding is carried out.

Of course, without prejudice to the principle of the invention, the details of construction and embodiment may be widely varied with respect to those described and illustrated without departing from the scope of the invention as defined by the claims that follow.

The invention claimed is:

1. Apparatus for producing a composite elasticized web with intermittent elastic sections, comprising:
   a tensioning unit for tensioning in a longitudinal direction a continuous elastic film;
   a cutting and repitch unit comprising a knife roller and a rotary repitch device comprising a plurality of transport units and a plurality of anvils cooperating with the knife roller for transversely cutting the continuous tensioned elastic film and forming a succession of discrete sections of elastic film, wherein the transport units hold by suction respective discrete sections of elastic film and distance them from each other by a predetermined pitch;
   a welding unit comprising an anvil roller and a welding head cooperating with the anvil roller, wherein the anvil roller has at least one suction section including a plurality of suction holes connected to a source of sub-atmospheric pressure and a plurality of projecting teeth cooperating with said suction holes and having head surfaces forming counter-welding surfaces which cooperate with said welding head;
   a tangency zone between the transport unit and the anvil roller in which the respective discrete sections of elastic film are transferred to said at least one suction section of the anvil roller;
   a first feeding system for feeding a first web material to the anvil roller upstream of said tangency zone; and
   a second feeding system for feeding a second web material to the anvil roller between said tangency zone and said welding head.

2. Apparatus according to claim 1, wherein said projecting teeth have a rhomboidal cross section.

3. Apparatus according to claim 1, wherein said suction holes and said teeth are arranged in transverse rows, wherein in each transverse row the suction holes and the projecting teeth alternate with each other.

4. A method for producing a composite elasticized web with intermittent elastic sections, comprising:
   tensioning in a longitudinal direction a continuous elastic film;
   cutting in the transverse direction the continuous elastic film and forming successive discrete portions of elastic film tensioned in the longitudinal direction;
   spacing from each other said discrete sections of elastic film at a predetermined pitch;
   transferring said discrete sections of tensioned elastic film on an anvil roller of a welding unit having at least one suction section provided with suction holes and with projecting teeth having head surfaces forming counter-welding surfaces;
   feeding to the anvil roller a first and a second continuous web material on opposite sides with respect to said discrete sections of elastic film; and
   welding to each other said first continuous web material, said discrete sections of tensioned elastic film and said second continuous web material on said head surfaces of said protruding teeth.

5. A method according to claim 4, wherein at least one of said first and second continuous web material is a non-woven web.

* * * * *